US005227638A

United States Patent [19]

Mizushima et al.

[11] Patent Number: 5,227,638

[45] Date of Patent: Jul. 13, 1993

[54] METHOD AND APPARATUS FOR EVALUATING LUMINOUS EFFICIENCY

[75] Inventors: Yoshihiko Mizushima; Takashi Iida; Eiji Inuzuka, all of Shizuoka, Japan

[73] Assignee: Hamamatsu Photonics K.K., Shizuoka, Japan

[21] Appl. No.: 737,795

[22] Filed: Jul. 24, 1991

Related U.S. Application Data

[63] Continuation of Ser. No. 519,752, May 7, 1990, abandoned.

[30] Foreign Application Priority Data

May 10, 1989 [JP] Japan ................................ 1-116748

[51] Int. Cl.[5] ............................................ H01L 33/00

[52] U.S. Cl. .............................. 250/484.1; 250/458.1; 250/459.1

[58] Field of Search ..................... 250/483.1, 484.1 R, 250/459.1, 458.1

[56] References Cited

U.S. PATENT DOCUMENTS 4,827,318 5/1989 Hall et al. .............................. 357/1

OTHER PUBLICATIONS

Black et al., "Scanned-Laser Microscope For Photoluminescence Studies", Applied Optics, vol. 11, No. 7, Jul. 1972, pp. 1553-1562.

Stadler et al., "A Technique For Measuring the Saturation of Phosphors at High Current Densities", J. Electrochem. Soc., vol. 120, No. 12, Dec. 1973, pp. 1730-1734.

Love et al., "Fluorescence Quantum Yield Determination By Pulsed Source Single Photon Counting", Analytical Chem, vol. 51, No. 12, Oct. 1979, pp. 1941-1945.

*Primary Examiner*—Constantine Hannaher
*Assistant Examiner*—Edward J. Glick
*Attorney, Agent, or Firm*—Finnegan, Henderson, Farabow, Garrett & Dunner

[57] ABSTRACT

Photoluminescence or electroluminescence from a material substrate is measured in a photon-counting range. Luminous efficiency of the substrate in its normal operation range is evaluated on the basis of the measured data. The luminescence is measured in an excitation range of the material including a transition excitation level corresponding to a transition luminous level from a low luminous range to a regular, intense luminous range. Two-dimensional distribution of the luminous efficiencies can be obtained by measuring the luminescence from small divided areas of the substrate.

11 Claims, 1 Drawing Sheet

Old Green
New Green
LED Current (A) (Excitation Quantity)
Light Power (W) (Luminous Quantity)
$10^{-9}$
$10^{-8}$
$10^{-7}$
$10^{-6}$
$10^{-5}$
$10^{-4}$
$10^{-3}$
$10^{-2}$
$10^{-1}$
$10^{0}$
$10^{-3}$
$10^{-6}$
$10^{-9}$
$10^{-12}$
$10^{-15}$

METHOD AND APPARATUS FOR EVALUATING LUMINOUS EFFICIENCY

This application is a continuation of application Ser. No. 07/519,752 filed May 7, 1990, abandoned.

BACKGROUND OF THE INVENTION

The present invention relates to a method and apparatus for evaluating luminous efficiency, sometimes referred to as relative quantum yield, which is applied for evaluating quality such as distribution of defects in a semiconductor substrate for, e.g., GaAs light-emitting diodes.

The quality evaluation of the luminous efficiency of, for example, a material substrate for GaAs light-emitting diodes (LEDs) is indispensable for the improvement of the luminous efficiency and the production yield of the LEDs. For laser diodes, the same is also necessary for the reduction and uniformity of their oscillation threshold.

Conventionally, test diodes that are formed from part of a substrate are used for the luminous efficiency evaluation. To determine the defects of distribution, irregularity, etc. over the entire substrate, a luminous quantity from the entire substrate is measured by a photoluminescence method.

The luminous efficiency evaluation method using the test diodes is capable of evaluating the luminous efficiency of the part of the substrate from which the test diodes are formed, but is not sufficient to evaluate the entire substrate. It is certain that there exists defects of distribution, irregularity, etc. in one substrate. However, this method cannot provide such information.

As for the method of measuring the luminous quantity from the entire substrate by the photoluminescence method in order to determine the defects of distribution, irregularity, etc. over the entire substrate, there is no available method which can present data on the luminous efficiency of the actual products.

SUMMARY OF THE INVENTION

Accordingly, an object of the present invention is to provide a method and apparatus for evaluating luminous efficiency, which can provide reliable information on the defects of distribution, irregularity, etc. over the entire material substrate.

In a method and apparatus for evaluating luminous efficiency of a material, according to a first aspect of the invention, photoluminescence or electroluminescence from the material is measured in a photon-counting range. The luminous efficiency of the material in its normal operation range is evaluated on the basis of the measured data.

According to a second aspect of the invention, photoluminescence or electroluminescence from the material is measured in at least two ranges including both of a photon-counting range and a regular, intense luminous range. The luminous efficiency of the material is evaluated by comparing the measured data.

A two-dimensional distribution image of luminous efficiencies can be obtained by performing a two-dimensional mapping between luminous efficiency data and small divided areas of the material.

DETAILED DESCRIPTION OF THE INVENTION

Figure 1:
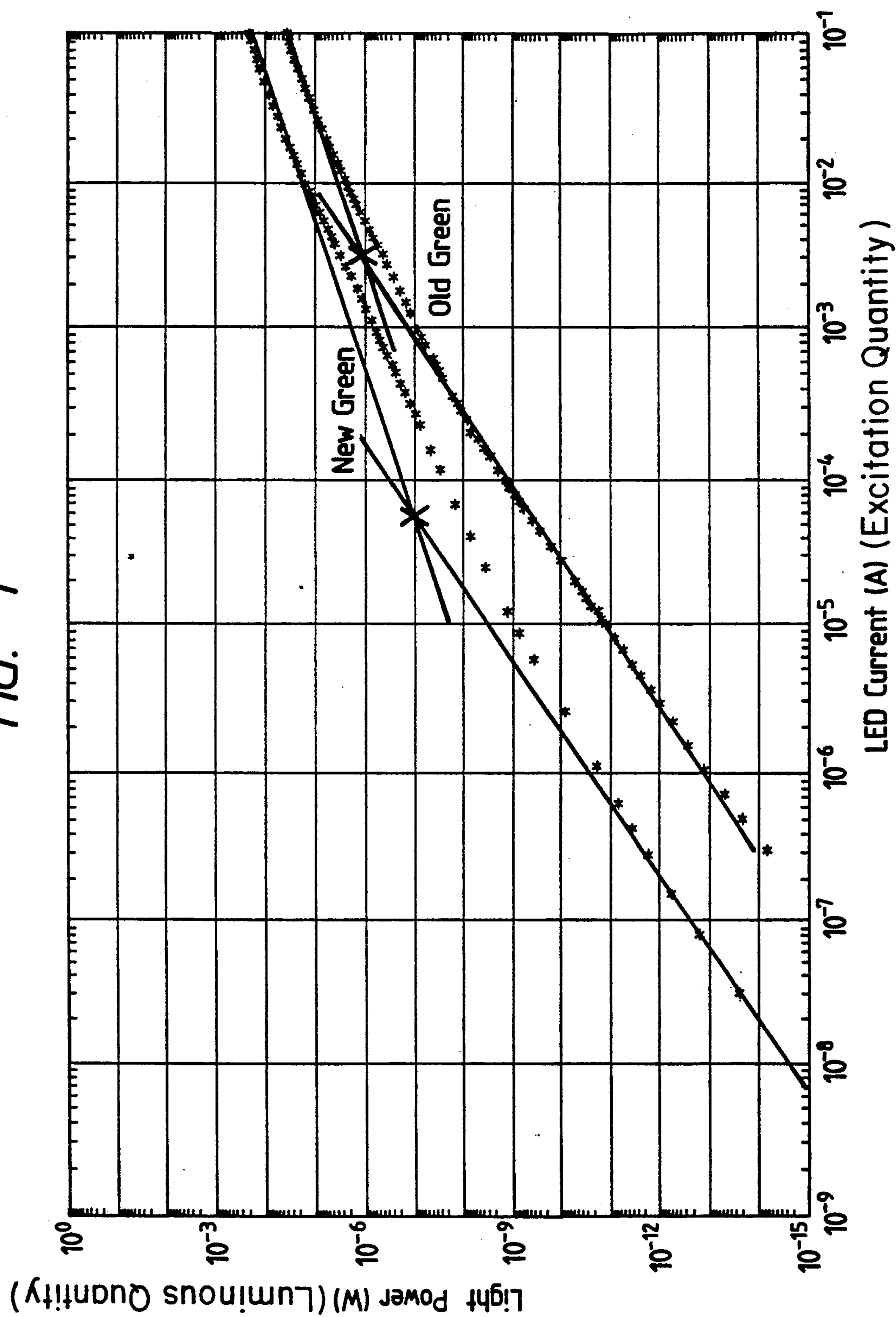
FIG. 1 is a graph showing a relationship between luminous intensity and LED current of two typical LEDs in a low excitation range.

In studying the above-described problems of the prior art, the present inventors discovered the following new facts.

In a low excitation range, a relationship between luminous quantity and excitation quantity is not linear, but the former is in proportion to a power of the latter (superlinear). This fact could be interpreted as follows. Many emission killer levels to prevent light emission exist in a material. Minority carriers generated upon excitation are trapped by those killer levels, in an initial stage. Accordingly, the luminous intensity is proportional to about the second power of the excitation quantity. Transition to a regular, intense luminous range is not done until those levels are filled with carriers.

The fact of great interest here is that the lower the transition point is, the higher the efficiency of regular luminescence. This fact implies that the luminous efficiency of a material can be evaluated by performing measurements even in a low excitation range in the vicinity of the transition point, instead of performing a measurement in a regular luminous operation range as in the conventional evaluation method.

In other words, since the weak excitation needs only a short period of excitation, the measurement time can be reduced. The distribution of luminous efficiencies of a material substrate can be measured with weak excitation for each of small divided areas corresponding to respective picture elements, not by illuminating the entire substrate. This facilitates the measurement of a large area of a substrate.

The present invention is based on the facts described above. Electric excitation or optical excitation in the low excitation range is applied to a semiconductor substrate, which in turn emits weak light. The emitted weak light is received and measured by a suitable means. With this method, only the levels preventing the luminesence itself can be directly picked up, and the evaluation is performed on the basis of such detection. This is one of the advantages of the invention.

The detailed method of operation is now explained.

To evaluate the relative quantum yield of a luminous material, the luminous material is excited with an electric or optical excitation in the low excitation range to emit luminescence. The luminescence from the luminous material is measured in the photon-counting range. The measurement is stopped once a transition point has been reached. The transition point, as discussed earlier, is a point in which a relationship between a luminous quantity and an excitation quantity of the luminous material transitions from a non-linear relationship, where the range of excitation is a low range, to a linear relationship, where the range of excitation is a regular, intense luminous range. The relative quantum yield of the luminous material is evaluated for the normal operation range based on the measured data from the photon counting range.

Another method may be used to evaluate the relative quantum yield of a luminous material. In this method, the luminous material is excited as discussed above. However, the luminescence from the luminous material is measured both in the photon-counting range and in the regular, intense luminous range. From this measured data, the transition point is determined. The relative quantum yield of the luminous material is evaluated based on the measured data from the transition point in which a transition point at a lower portion of the measured data allows a higher efficiency of regular luminescence.

To effect the evaluation according to the present invention, it is necessary to use a photodetecting system which is sensitive enough to weak light. A photon-counting device is preferable for such a photodetecting system.

The measurements of luminous intensities of a semiconductor substrate in the photon-counting range make it possible to straightforwardly predict the quality of products from the substrate. The intensities thus measured are much smaller than those as predicted by extrapolating data in the weak luminous range from data in the normal operation range. Therefore, the photon-counting method is required in the invention.

FIG. 1 shows a relationship between the luminous intensity (i.e., light power) and the LED current of two typical LEDs as measured in the low excitation range. The graph shows that, in the low excitation range, the slope of the curves is almost 2 in the logarithmic representation. Furthermore, in this graph, the new green LED, whose luminous intensity is higher in the normal luminous range, has the transition point, evaluated by a device 6 for evaluating the transition point as shown in FIG. 2, transition point at the lower side of excitation.

It is noted that where a sample has a size equivalent to that of an ordinary LED, the photon-counting method is used for measuring the luminous intensity in the low excitation range. The photon-counting method is a key method in the measurement in the low excitation range, except for a sample of large area. The same thing is true for the measurement in which two-dimensional distribution of luminous efficiencies are measured by dividing those so as to be in correspondence with respective small picture element areas.

As described above, the evaluation method and apparatus of the invention realizes non-contact, non-invasive evaluation of the luminous efficiency of a material substrate used for LEDs or laser diodes, and also the similar luminous efficiency evaluation of a plurality of areas in one substrate.

What is claimed is:

1. A method for evaluating a relative quantum yield of a luminous material, comprising the steps of:
   exciting the luminous material to emit luminescence;
   measuring luminescence from the luminous material in a photon-counting range, wherein said measuring luminescence is stopped once a transition point has been reached, said transition point being a point in which a relationship between a luminous quantity of the luminous material and an excitation quantity transitions from a non-linear relationship, where the range of excitation is a low range, to a linear relationship, where the range of excitation is a regular, intense luminous range; and
   evaluating the relative quantum yield of the luminous material in a normal operation range based on the measuring step.

2. The method according to claim 1, wherein the luminescence is photoluminescence.

3. The method according to claim 1, wherein the luminescence is electroluminescence.

4. The method according to claim 1, further comprising the step of performing two-dimensional mapping between relative quantum yield data obtained in the evaluating step and small divided areas of the luminous material to obtain a two-dimensional distribution image of the relative quantum yields of the luminous material.

5. The method according to claim 1, wherein the luminous material is a semiconductor substrate.

6. The method according to claim 1, wherein the luminous quantity is proportional to about a second power of the excitation quantity.

7. A method for evaluating a relative quantum yield of a luminous material, comprising the steps of:
   exciting the luminous material to emit luminescence;
   measuring luminescence from the luminous material in at least two ranges including both of a photon-counting range and a regular, intense luminous range;
   determining a transition point between said luminescence of said photon-counting range and said regular, intense luminous range by comparing data obtained from both of said ranges, wherein said transition point is a point in which a relationship between a luminous quantity of the luminous material and an excitation quantity transitions from a non-linear relationship, where the range of excitation is a low range, to a linear relationship, where the range of excitation is a regular, intense luminous range; and
   evaluating the relative quantum yield of the luminous material from the transition point obtained in the determining step.

8. The method according to claim 7, wherein the luminescence is photoluminescence.

9. The method according to claim 7, wherein the luminescence is electroluminescence.

10. The method according to claim 7, further comprising the step of performing two-dimensional mapping between relative quantum yield data obtained in the evaluating step and small divided areas of the luminous material to obtain a two-dimensional distribution image of the relative quantum yields of the luminous material.

11. The method according to claim 7, wherein the luminous material is a semiconductor substrate.

* * * * *